US010123700B2

(12) United States Patent
Nakajima

(10) Patent No.: US 10,123,700 B2
(45) Date of Patent: Nov. 13, 2018

(54) OPHTHALMIC APPARATUS AND ALIGNMENT METHOD FOR OPHTHALMIC APPARATUS

(71) Applicant: TOPCON CORPORATION, Itabashi-ku, Tokyo (JP)

(72) Inventor: Masashi Nakajima, Tokyo (JP)

(73) Assignee: TOPCON CORPORATION, Itabashi-Ku, Tokyo (JP)

( * ) Notice: Subject to any disclaimer, the term of this patent is extended or adjusted under 35 U.S.C. 154(b) by 0 days.

(21) Appl. No.: 15/686,223

(22) Filed: Aug. 25, 2017

(65) Prior Publication Data

US 2018/0055358 A1 Mar. 1, 2018

(30) Foreign Application Priority Data

Aug. 26, 2016 (JP) ................................ 2016-165406

(51) Int. Cl.
*A61B 3/15* (2006.01)
*A61B 3/00* (2006.01)
*A61B 3/14* (2006.01)

(52) U.S. Cl.
CPC ............ *A61B 3/152* (2013.01); *A61B 3/0058* (2013.01); *A61B 3/0083* (2013.01); *A61B 3/14* (2013.01); *A61B 3/15* (2013.01)

(58) Field of Classification Search
CPC .. A61B 3/152; A61B 3/15; A61B 3/14; A61B 3/0083; A61B 3/0058
USPC .................................................. 351/206, 208
See application file for complete search history.

(56) References Cited

U.S. PATENT DOCUMENTS

| | | | | |
|---|---|---|---|---|
| 6,193,371 B1 * | 2/2001 | Snook | A61B 3/1005 | 351/212 |
| 6,257,722 B1 * | 7/2001 | Toh | A61B 3/152 | 351/208 |
| 2004/0143246 A1 * | 7/2004 | Maeda | A61F 9/008 | 606/5 |
| 2008/0018855 A1 * | 1/2008 | Larichev | A61B 3/032 | 351/211 |

(Continued)

FOREIGN PATENT DOCUMENTS

| | | |
|---|---|---|
| JP | 2013-248376 A | 12/2013 |
| JP | 2014113385 A | 6/2014 |
| JP | 2014-124370 A | 7/2014 |

*Primary Examiner* — William R Alexander
(74) *Attorney, Agent, or Firm* — Chiesa Shahinian & Giantomasi PC

(57) ABSTRACT

An ophthalmic apparatus and method is provided for quickly and accurately aligning a measurement optical system with the vertex of the cornea of a subject's eye. The ophthalmic apparatus comprises a main body, an infrared detection system, a support portion, a driving unit, a visible light irradiation system placed coaxially with the apparatus main body and configured to irradiate the subject's eye, at least two photographing devices configured to substantially simultaneously photograph the subject's eye from different directions, a first alignment detection unit configured to acquire Purkinje images of the subject's eye, originating from infrared light, from at least two photographed images of the subject's eye and detect a position of the subject's eye from the Purkinje images, a second alignment detection unit, and a drive control unit to align the apparatus with the subject's eye.

8 Claims, 12 Drawing Sheets

(56) References Cited

U.S. PATENT DOCUMENTS

2011/0273669 A1* 11/2011 Abitbol ................ A61B 3/1015
351/212

* cited by examiner

OPHTHALMIC APPARATUS AND ALIGNMENT METHOD FOR OPHTHALMIC APPARATUS

CROSS-REFERENCE TO RELATED APPLICATION

This application is based upon and claims the benefit of priority from Japanese Patent Application No. 2016-165406, filed Aug. 26, 2016, the entire contents of which are incorporated herein by reference.

TECHNICAL FIELD

The present invention relates to an ophthalmic apparatus for acquiring data about subject's eyes and an alignment method for the ophthalmic apparatus.

BACKGROUND OF THE INVENTION

An ophthalmic apparatus includes an ophthalmic measurement apparatus for measuring the properties of a subject's eye and an ophthalmic photographing apparatus for obtaining an image of the subject's eye.

Examples of ophthalmic measurement apparatuses include ocular refraction examination apparatuses (refractometers and keratometers) which measure the refractive properties of subject' eyes, tonometers, specular microscopes for obtaining corneal properties (for example, corneal thicknesses and corneal endothelial cell densities), and wavefront analyzers for obtaining the aberration information of subject's eyes by using Hartmann-Shack sensors.

In addition, examples of ophthalmic photographing apparatuses include optical interferometry tomographic apparatuses for obtaining tomographic images by using optical coherence tomography (OCT), fundus cameras for photographing the fundi, and scanning laser ophthalmoscopes (SLOs) for obtaining images of the fundi by laser scanning using confocal optical systems.

In ophthalmic examinations using such apparatuses, alignment between an optical system and the subject's eye is important in terms of examination precision and accuracy. Examples of alignment generally include the operation (XY alignment) of aligning the subject's eye with the optical axis of an optical system and the operation (Z alignment) of adjusting the distance between the subject's eye and the optical system to a predetermined operating distance.

Some of such alignment techniques are designed to execute XY alignment and Z alignment based on pupil images captured by stereo cameras (patent literature 1 (Japanese Patent Laid-Open No. 2013-248376), patent literature 2 (Japanese Patent Laid-Open No. 2014-113385), and patent literature 3 (Japanese Patent Laid-Open No. 2014-124370)). Alignment using such a stereo camera covers a wide alignment range, requires no manual alignment, and allows automatic alignment in most cases.

In alignment using a conventional stereo camera, however, because the distance between a reference position on the apparatus and the pupil is set as a reference, the vertex of the cornea cannot be positioned due to individual differences in anterior chamber depth. Although patent literature 3 discloses a study on a method of correcting the depth position information of a cornea image using corneal refractive power, it is necessary to separately provide a mechanism for measuring the curvature of the cornea to obtain a corneal refractive power.

The stereo camera method as operating distance alignment means is influenced by individual differences in anterior chamber depth, corneal curvature, and the like, and hence cannot be used for devices requiring alignment with respect to the vertex of the cornea.

SUMMARY OF THE INVENTION

The present invention has been made in consideration of the above problem, and has as its object to provide an ophthalmic apparatus which can quickly and accurately align a measurement optical system with the vertex of the cornea of a subject's eye and an alignment method for the ophthalmic apparatus.

According to a first aspect of the present invention which solves the above problem, there is provided an ophthalmic apparatus comprising an apparatus main body including an infrared irradiation system configured to irradiate a subject's eye with infrared light and an infrared detection system configured to detect the infrared light from the subject's eye, a support portion configured to support a position of the face of a subject, a driving unit configured to align an axis of the apparatus main body with the subject's eye and also perform distance adjustment of the apparatus main body to the subject's eye by relatively moving the apparatus main body and the support portion, a visible light irradiation system placed coaxially with the apparatus main body and configured to irradiate the subject's eye with visible light, not less than two photographing devices configured to substantially simultaneously photograph the subject's eye from different directions, a first alignment detection unit configured to acquire Purkinje images of the subject's eye from not less than two photographed images of the subject's eye, originating from the infrared light, from not less than two photographed images of the subject's eye obtained by the two photographing devices and detect a position of the subject's eye from the Purkinje images, a second alignment detection unit configured to acquire a scattered light image of a cornea of the subject's eye, originating from the visible light, obtained by at least one of the two photographing devices and detect the vertex of the cornea based on the scattered light image, and a drive control unit configured to align the apparatus main body with the subject's eye by controlling the driving unit based on a detection result obtained by the first alignment detection unit and also perform distance adjustment or alignment and distance adjustment of the apparatus main body with respect to the subject's eye by controlling the driving unit based on a detection result obtained by the second alignment detection unit.

According to a second aspect of the present invention, the scattered light image of the cornea is acquired by one of the not less than two photographing devices.

According to a third aspect of the present invention, at least one photographing device of the not less than two photographing devices has a larger photographing magnification than another or other photographing devices.

According to a fourth aspect of the present invention, the photographing device comprises a transmission filter configured to transmit the infrared light.

According to a fifth aspect of the present invention, the photographing device, of the photographing devices, which obtains the scattered light image of the cornea comprises a transmission filter configured to transmit the infrared light and the visible light.

According to a sixth aspect of the present invention, the infrared irradiation system is configured to change an intensity of infrared light for irradiation.

According to a seventh aspect of the present invention, the visible light irradiation system is configured to change an intensity of visible light for irradiation.

According to an eighth aspect of the present invention, there is provided an alignment method for an ophthalmic apparatus which includes an apparatus main body configured to irradiate a subject's eye with infrared light and also detect the infrared light from the subject's eye, a support portion configured to support a position of the face of a subject, and a driving unit configured to relatively move the apparatus main body and the support portion, aligns the apparatus main body with the subject's eye by relatively moving the apparatus main body and the support portion, and performs distance adjustment with respect to the subject's eye, the method comprising a step of detecting Purkinje images of the subject's eye by substantially simultaneously photographing a cornea of the subject's eye from not less than two different directions by irradiating the subject's eye with infrared light, a step of aligning the apparatus main body with the subject's eye based on positions of the Purkinje images, a step of detecting a scattered light image of the cornea, originating from visible light which has irradiated the subject's eye, and a step of performing distance adjustment or alignment and distance adjustment of the apparatus main body with respect to the subject's eye based on the vertex of the cornea of the subject's eye detected based on the scattered light image.

The present invention can quickly and accurately align the apparatus main body with the vertex of the cornea of the subject's eye.

That is, the ophthalmic apparatus according to the first aspect acquires Purkinje images of the subject's eye from two or more photographed images of the subject's eye, originating from infrared light, obtained by two photographing devices, and aligns the apparatus main body with the subject's eye based on the Purkinje images. The apparatus then detects the position of the cornea based on a scattered light image of the cornea of the subject's eye, originating from visible light, obtained by at least one of the two photographing devices, and performs distance adjustment or distance adjustment and alignment of the apparatus main body with respect to the subject's eye. The ophthalmic apparatus can therefore perform alignment based on the directly detected vertex of the cornea of the subject's eye, and need not consider differences in anterior chamber depth or corneal curvature among subjects.

The ophthalmic apparatus according to the second aspect detects a scattered light image of the cornea using one photographing device, and hence can perform processing at high speed. In addition, because another or other photographing devices need not be provided with any equipment for visible light photography, an inexpensive ophthalmic apparatus can be provided.

In the ophthalmic apparatus according to the third aspect, at least one photographing device has a larger magnification than another or other photographing devices, and hence a scattered light image of the cornea can be acquired by the photographing device with the larger magnification. This makes it possible to accurately acquire the position of the vertex of the cornea.

In the ophthalmic apparatus according to the fourth aspect, because each photographing device is provided with a transmission filter for transmitting only infrared light, it is possible to prevent any false detection caused by external light different in wavelength from irradiation light.

In the ophthalmic apparatus according to the fifth aspect, because the photographing device for obtaining a scattered light image of the cornea is provided with a transmission filter for transmitting only infrared light and visible light, it is possible to prevent any false detection caused by external light different in wavelength from irradiation light.

The ophthalmic apparatus according to the sixth aspect can apply infrared light with a proper intensity for the detection of Purkinje images by changing the intensity of infrared light.

The ophthalmic apparatus according to the seventh aspect can apply visible light with a proper intensity for the detection of a scattered light image of the cornea by changing the intensity of visible light.

The alignment method for the ophthalmic apparatus according to the eighth aspect acquires Purkinje images of the subject's eye from two or more photographed images of the subject's eye, originating from infrared light, obtained by two photographing devices, and aligns the apparatus main body with the subject's eye based on the Purkinje images. The method then detects the position of the cornea based on a scattered light image of the cornea of the subject's eye, originating from visible light, obtained by at least one of the two photographing devices, and performs distance adjustment or distance adjustment and alignment of the apparatus main body with respect to the subject's eye. The ophthalmic apparatus can therefore perform alignment based on the directly detected vertex of the cornea of the subject's eye, and need not consider differences in anterior chamber depth or corneal curvature among subjects.

BRIEF DESCRIPTION OF THE DRAWINGS

FIGS. 1A and 1B show the outer appearance of a non-contact tonometer according to an embodiment of the present invention, in which FIG. 1A is a front view and FIG. 1B is a side view showing a use state;

FIGS. 2A and 2B are schematic views showing the internal arrangement of the non-contact tonometer, in which FIG. 2A is a side view and FIG. 2B is a plan view;

FIGS. 8A and 8B are views for explaining photographed images acquired by the non-contact tonometer, in which FIG. 8A is a schematic view for explaining Purkinje images and FIG. 8B is a schematic view for explaining a scattered light image of the cornea;

DESCRIPTION OF THE EMBODIMENTS

An ophthalmic apparatus and an alignment method for the ophthalmic apparatus according to an embodiment for carrying out the present invention will be described. The present invention can be applied to an arbitrary ophthalmic measurement apparatus and an arbitrary ophthalmic photographing apparatus or composite apparatus. That is, the present invention can be applied to a refractometer, keratometer, specular microscope, tonometer, or the like as an ophthalmic measurement apparatus. The present invention can also be applied to an optical coherence tomography (OCT) apparatus, fundus camera, scanning laser ophthalmoscope (SLO), or the like as an ophthalmic photographing apparatus.

A non-contact tonometer will be described as an example of an ophthalmic apparatus according to an embodiment.

<Schematic Arrangement of Non-Contact Tonometer>

Figure 1A:
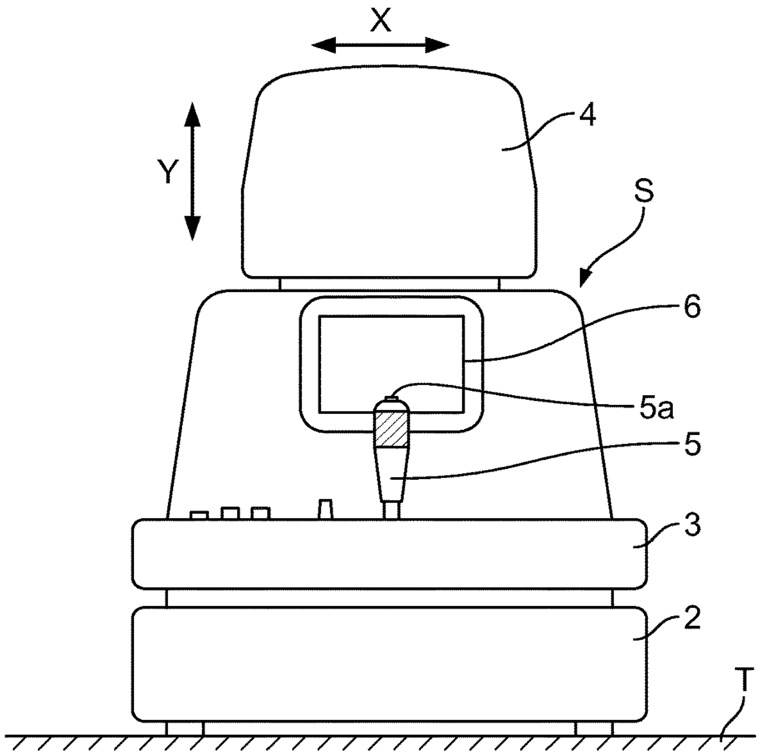
Figure 1B:
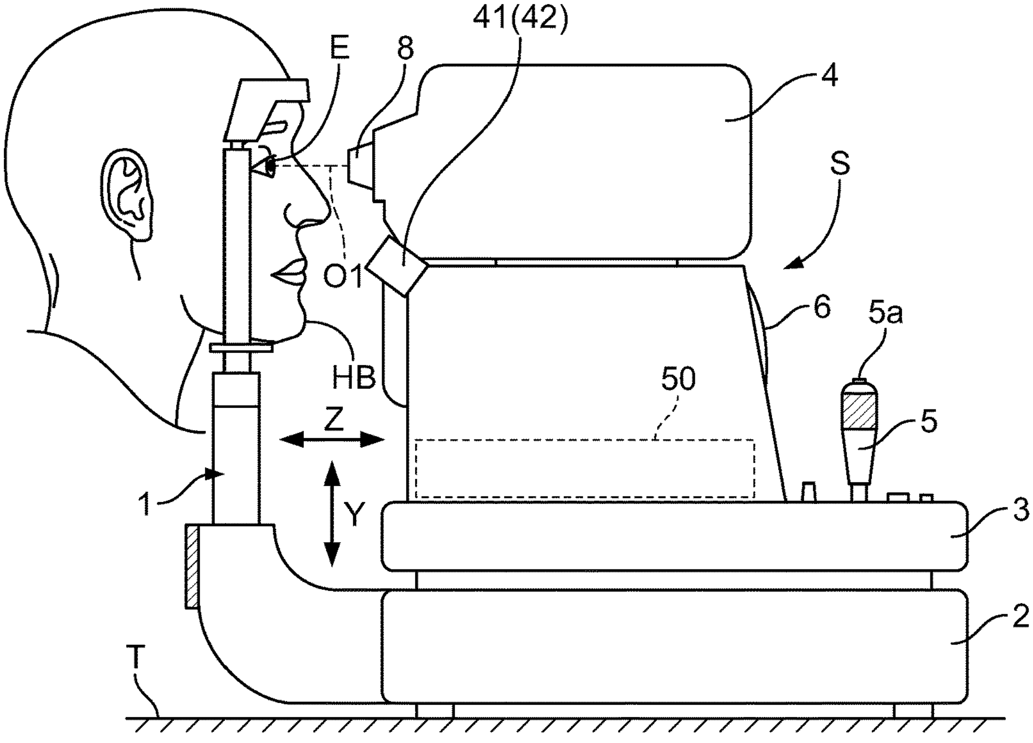

FIGS. 1A and 1B show the outer appearance of a non-contact tonometer according to an embodiment of the present invention, in which FIG. 1A is a front view and FIG. 1B is a side view showing a use state. A non-contact tonometer S includes a support portion 1, an apparatus base 2, a mount 3, and an apparatus main body 4.

The support portion 1 is placed on the apparatus base 2 and supports a face HB of a subject. The apparatus base 2 has the support portion 1. The apparatus base 2 is placed on an installation table T. The mount 3 is placed on the apparatus base 2. The mount 3 is provided to be movable relative to the apparatus base 2 in the longitudinal and lateral directions. Note that the longitudinal direction (the direction along the optical axis of the non-contact tonometer S) is defined as the Z direction, and the lateral and vertical directions perpendicular to the optical axis are respectively defined as the X and Y directions.

The apparatus main body 4 is provided on the mount 3, and is moved relative to the mount 3 in the Z, X, and Y directions through the operation of an internal driving unit 50. Note that the apparatus main body 4 may be structured to move together with the mount 3, instead of independently moving, in the Z, X, and Y directions.

The mount 3 is provided with an operation knob 5 having a measurement button 5*a*, a monitor 6, and the like. The examiner operates the operation knob 5 to move the mount 3 back and forth, right and left, and up and down. In this case, tilting the operation knob back and forth and right and left will move the apparatus main body 4 back and forth and right and left, and rotating the operation knob itself about its axis will move the apparatus main body 4 up and down. The front surface of the apparatus main body 4 is provided with an air puff nozzle 8 extending through an anterior eye window glass 12 (see FIGS. 2A and 2B) so as to face a subject's eye E of a subject. In addition, the function of the operation knob 5 may be implemented by using the touch panel of the monitor 6, an external mouse, or the like.

<Internal Arrangement of Non-Contact Tonometer>

Figure 2A:
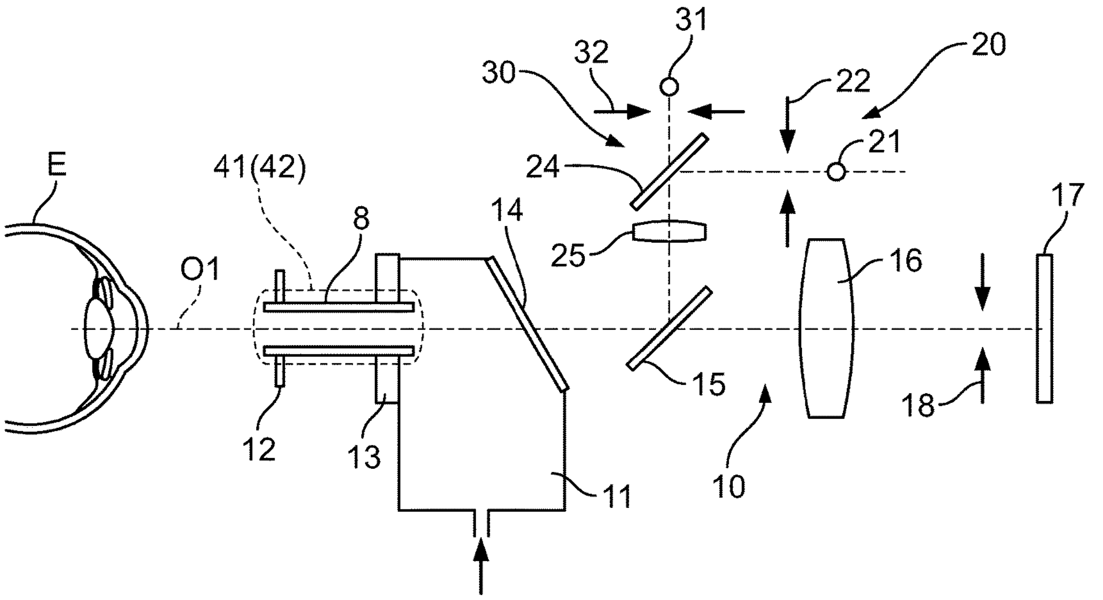
Figure 2B:
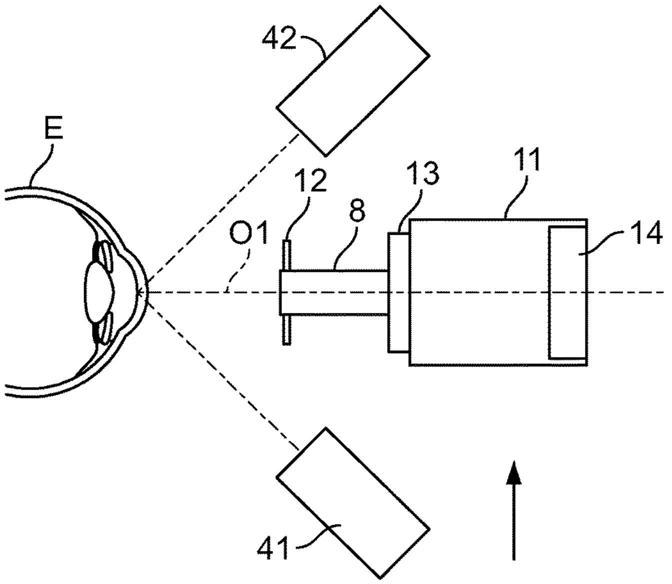

FIGS. 2A and 2B are schematic views showing the internal arrangement of the non-contact tonometer, in which FIG. 2A is a side view and FIG. 2B is a plan view. The apparatus main body 4 accommodates an air chamber 11, an intraocular pressure measurement system 10 which is an infrared detection system, an infrared irradiation system 20, and a visible light irradiation system 30. In this embodiment, two face cameras 41 and 42 are arranged on the apparatus main body 4. These two cameras serve as two photographing devices located on both sides of an axis O1 in the Y direction. Note that the face cameras 41 and 42 include infrared sources for irradiating the subject's eye E with infrared light. The face cameras 41 and 42 substantially simultaneously photograph the subject's eye from different directions. In this case, "substantially simultaneously" indicates that photographing timing differences small enough to ignore eye movements are permitted in photography by the face cameras 41 and 42. This allows two or more anterior eye cameras to acquire images of the subject's eye E at the same position.

An air spray device 60 sends air to the air chamber 11. The sent air is puffed from the air puff nozzle 8 to the subject's eye E. Note that referring to FIGS. 2A and 2B, reference numeral 12 denotes an anterior eye window glass; and 13 and 14, chamber glasses. The air spray device 60 (see FIG. 3) is connected to the air chamber 11. The air spray device 60 compresses air in a cylinder by a piston driven by a solenoid, and feeds the compressed air to the air chamber 11.

The optical axis of the intraocular pressure measurement system 10, the infrared irradiation system 20, and the visible light irradiation system 30 is placed behind the air chamber 11. The optical axis of the intraocular pressure measurement system 10, the infrared irradiation system 20, and the visible light irradiation system 30 is placed in the air puff nozzle 8. A chamber window glass 14 is placed in the air chamber 11. The axis O1 of the intraocular pressure measurement system 10, the infrared irradiation system 20, and the visible light irradiation system 30 extends through the chamber window glass 14. The chamber window glass 14 is placed obliquely at a predetermined angle relative to the axis O1 to eliminate the influence of light reflection.

<Optical System of Non-Contact Tonometer>

As shown in FIG. 2A, the intraocular pressure measurement system 10 includes a first dichroic mirror 15, an imaging lens 16, an applanation sensor 17 formed from an infrared sensor, and a pinhole 18. The infrared irradiation system 20 includes an infrared source 21 and a stop 22. The visible light irradiation system 30 includes a visible light source 31 of, for example, blue light, and a stop 32. The infrared irradiation system 20 is coupled to the visible light irradiation system 30 through a second dichroic mirror 24. A collimator lens 25 collimates light into parallel light. The parallel light is then guided to the first dichroic mirror 15 and applied from the air chamber 11 to the subject's eye E through the air puff nozzle 8.

In this embodiment, the infrared source 21 of the infrared irradiation system 20 irradiates the subject's eye E with an infrared light spot with a diameter of about 3 mm. The applanation sensor 17 detects reflected light from the subject's eye E. When the air puff nozzle 8 puffs air to the subject's eye E, a change in the amount of reflected light is measured based on the change in corneal shape detected by the applanation sensor 17, thereby measuring an intraocular pressure. In this embodiment, the infrared irradiation system 20 is used both for intraocular pressure measurement and for the alignment of the non-contact tonometer S which is performed by making the face cameras 41 and 42 photograph the subject's eye E irradiated with infrared light from the infrared irradiation system 20. For this purpose, the luminance of the infrared source 21 can be changed.

In the infrared irradiation system 20, the second dichroic mirror 24 reflects infrared light from the infrared source 21 after transmission through the stop 22, and the collimator lens 25 then collimates the light into a parallel light beam.

The first dichroic mirror 15 reflects the light beam, which passes through the chamber window glass 14 and the air puff nozzle 8 and illuminates the cornea of the subject's eye E. Light beams from the infrared irradiation system 20 and the visible light irradiation system 30 are coaxially combined by the second dichroic mirror 24 to irradiate the subject's eye E.

Note that the second dichroic mirror 24 transmits wavelengths in the visible light range from the visible light irradiation system 30, and at the same, reflects wavelengths in the infrared range from the infrared irradiation system 20. The second dichroic mirror 24 has a dielectric multilayer having the above property. The first dichroic mirror 15 has the property of reflecting most of wavelengths in the visible light range while partially transmitting and partially reflecting wavelengths in the infrared range. The second dichroic mirror 24 is a multilayer mirror, and generally has a transmittance of 50% and a reflectance of 50%. However, this mirror may be configured to have low transmittance and high reflectance.

The infrared light reflected by the cornea of the subject's eye E passes through the inside of the air puff nozzle 8, the chamber window glass 14, and the first dichroic mirror 15, and is transmitted through the imaging lens 16 and the pinhole 18 to reach the applanation sensor 17. The applanation sensor 17 detects a change in the amount of infrared light reflected by the cornea and transmitted through the pinhole 18. This measures the intraocular pressure of the subject's eye E.

That is, the pressure of puffed air flattens and depresses the cornea. The pinhole 18 is placed to be conjugated with the light source through the imaging lens when the cornea is flattened. This lets the maximum amount of light be transmitted through the pinhole 18 and enter the applanation sensor 17 when the cornea is flattened as it changes from a convex surface to a concave surface through a flat surface. It is therefore determined that the cornea is flattened when the amount of light received by the applanation sensor 17 becomes maximum from the start of air puffing. In this case, the air chamber 11 accommodates a pressure instrument to detect the internal pressure of the air chamber 11. The pressure value detected when the above amount of light becomes maximum (the cornea is flattened) is measured as an intraocular pressure value.

The visible light irradiation system 30 irradiates the subject's eye E with visible light from the visible light source 31 as fixation light which becomes a fixed collimation, and also as light for acquiring a scattered light image for the detection of the vertex position of the cornea. In this embodiment, the subject's eye E is irradiated with the visible light within a range narrower than that irradiated with the above infrared light, and the visible light source 31 is designed to emit blue light in consideration of the light scattering property of the internal corneal tissue. In addition, the luminance of the visible light source 31 can be changed. The luminance of the visible light source 31 is increased when scattered light is acquired, compared with when light from the visible light source 31 is used as fixation light. Note that light emitted from the visible light source 31 is not limited to blue light and may be green light or the like. However, in consideration of the scattering property of the internal corneal tissue, blue light having a short wavelength is preferable.

The subject fixes his/her visual line to a measurement optical axis by fixing vision on an image of the visible light source 31 imaged at almost infinite distance. Note that irradiating the stop with light from the visible light source 31 can set the stop as a secondary light source.

<Control System for Non-Contact Tonometer>

Figure 3:
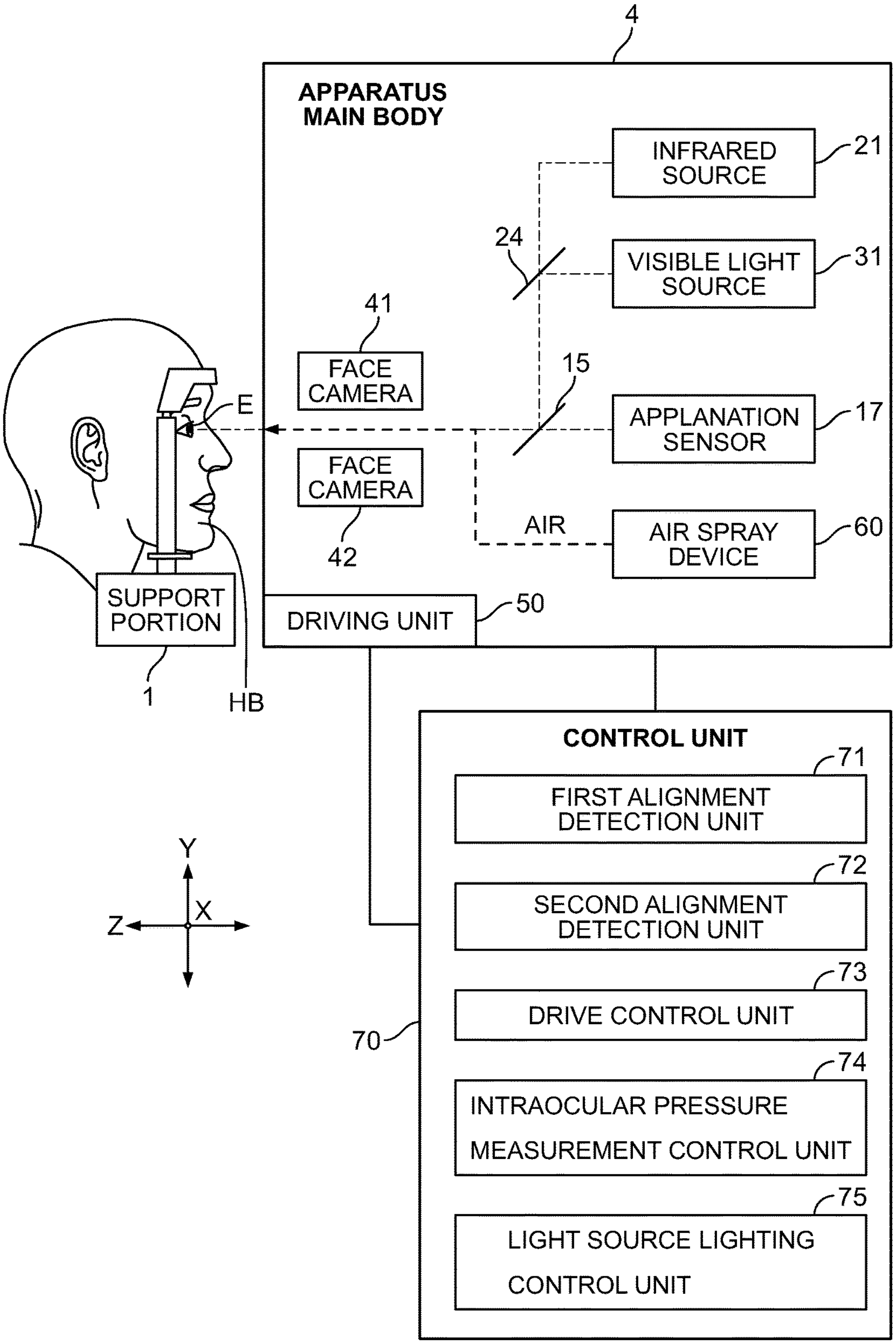
FIG. 3 is a block diagram showing a control system for the non-contact tonometer as an ophthalmic apparatus.

A control system for the non-contact tonometer S according to the embodiment will be described next. FIG. 3 is a block diagram showing a control system for the non-contact tonometer as an ophthalmic apparatus. The apparatus main body 4 incorporates the first dichroic mirror 15, the applanation sensor 17, the second dichroic mirror 24, the face cameras 41 and 42, the infrared source 21, the visible light source 31, the driving unit 50, and the air spray device 60, which have been described above.

A control unit 70 is connected to the apparatus main body 4. The control unit 70 includes a first alignment detection unit 71, a second alignment detection unit 72, a drive control unit 73, an intraocular pressure measurement control unit 74, and a light source lighting control unit 75.

The control unit 70 can be formed as a computer including a central processing unit (CPU) as a control means, a read only memory (ROM) as a main storage, a random access memory (RAM), and a hard disk drive (HDD) as an auxiliary storage. The CPU implements the functions of the above units by executing programs stored in the ROM using the RAM as an expansion area.

In the first alignment, the first alignment detection unit 71 detects the position of the subject's eye E relative to the apparatus main body 4, that is, the vertical and lateral positions (X, Y) and the longitudinal position (Z) of the subject's eye E, based on the Purkinje images acquired by the face cameras 41 and 42. The first alignment detection unit 71 detects such Purkinje images by performing noise removal, binarization, contour detection, centroid detection, and the like with respect to image data from the face cameras 41 and 42.

In the second alignment, the second alignment detection unit 72 detects the anterior end position of the cornea based on the scattered light images of the inside of the cornea acquired by the face cameras 41 and 42. The second alignment detection unit 72 detects the vertex of the cornea from the scattered light images by performing noise removal, binarization, contour detection, and the like with respect to image data from the face cameras 41 and 42.

In the first alignment, the drive control unit 73 performs alignment in the X and Y directions and distance adjustment in the Z direction by driving the driving unit 50 based on the detection result obtained by the first alignment detection unit 71. In the second alignment, the drive control unit 73 performs distance adjustment in the Z direction by driving the driving unit 50 based on the detection result obtained by the second alignment detection unit 72.

<Schematic Operation of Non-Contact Tonometer S>

Figure 4:
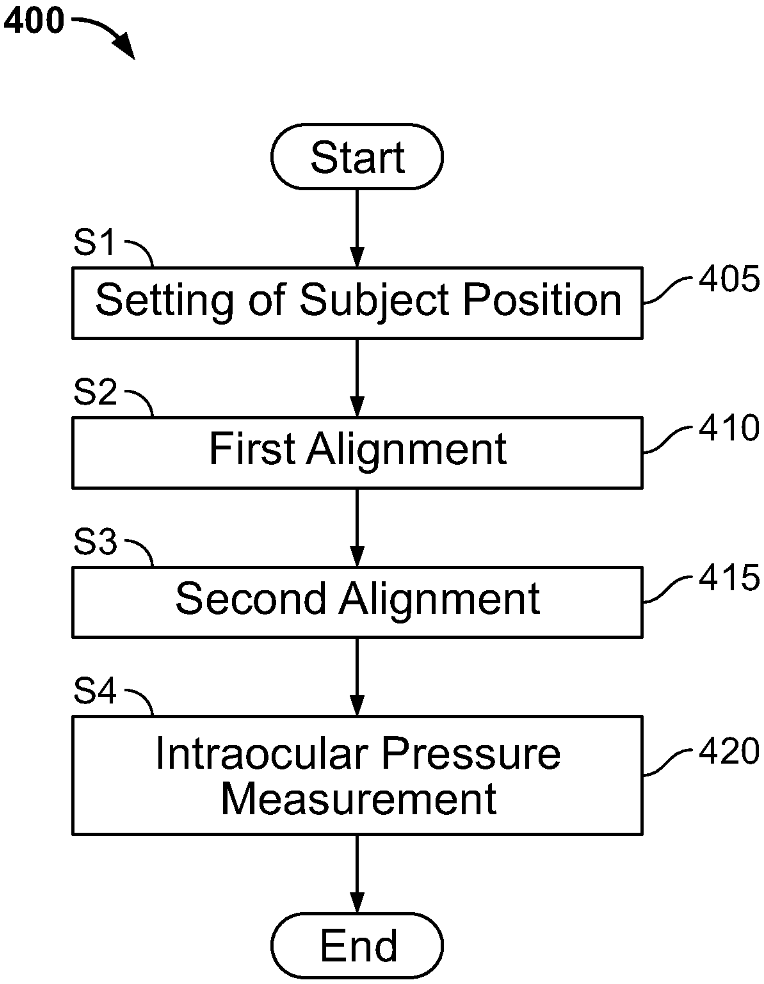
FIG. 4 is a flowchart showing a schematic operation procedure of the non-contact tonometer.

FIG. 4 is a flowchart 400 showing the basic operation procedure of the non-contact tonometer. In measuring the intraocular pressure of a subject by using the non-contact tonometer S according to this embodiment, first of all, the subject is positioned on the support portion 1 405 (also referred to herein as step S1). The first alignment 410 (also referred to herein as step S2) and the second alignment 415 (also referred to herein as step S3) are then performed. The distal end of the air puff nozzle 8 is aligned with the subject's eye E, and distance adjustment is performed with respect to the vertex of the cornea. Upon completion of alignment, intraocular pressure measurement is performed 420 (also referred to herein as step S4).

In the first alignment, the non-contact tonometer S according to this embodiment captures Purkinje images originating from infrared light from the infrared irradiation system 20 using the face cameras 41 and 42 which photograph the subject's eye E from different directions, and executes coarse alignment in the X, Y, and Z directions based on the captured Purkinje images. Upon completion of the first alignment, the non-contact tonometer S causes the apparatus main body 4 to retreat by a predetermined amount, and then captures scattered light inside the cornea, originating from visible light from the visible light irradiation system 30, using the face cameras 41 and 42. The non-contact tonometer S performs the second alignment of performing distance adjustment in the Z direction based on the scattered light images.

Figure 8A:
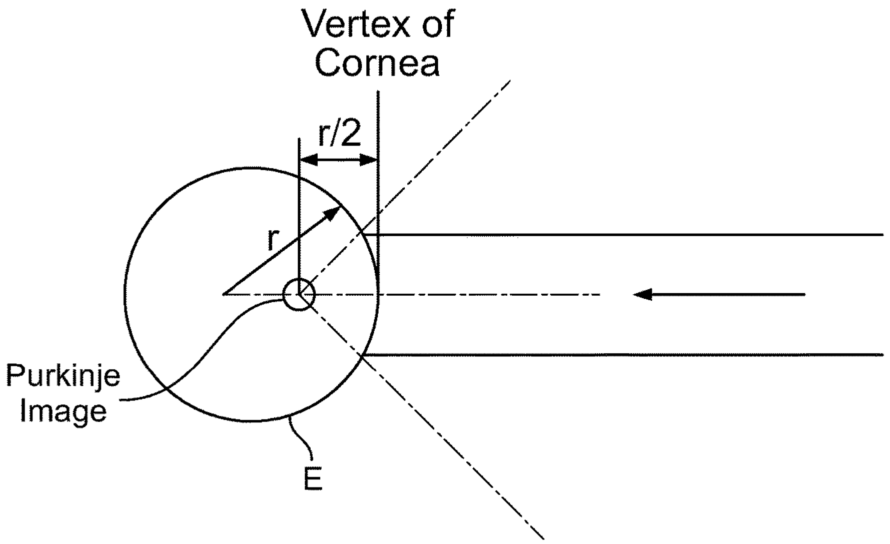

In this case, Purkinje images are reflection images obtained when the cornea, the crystalline lens, and the like reflect projected light. As shown in FIG. 8A, each Purkinje image obtained by irradiating the cornea with a parallel light beam and making the corneal surface reflect the light beam is a virtual image observed at a position corresponding to ½ of a corneal curvature radius r from the vertex of the cornea. The face cameras 41 and 42 acquire such images. Note that Purkinje images are a collective term of images formed by the reflection of light by the anterior and posterior surfaces of the cornea and the anterior and posterior surface of the crystalline lens, and are called, in a precise sense, the first, second, third, and fourth Purkinje images in order from the anterior surface side of the cornea. This embodiment uses the first Purkinje image formed by the reflection of light by the surface of the cornea.

Assume that in this embodiment, the retreat amount of the apparatus main body 4 before the first alignment is ½ of the average corneal curvature radius r. The average corneal curvature radius r can be 8 mm. The apparatus main body 4 is placed at a position retreated from the position set in the first alignment by 4 mm, thus switching to the second alignment. In this case, alignment in the X and Y directions is performed only by the first alignment.

The above description is made on the method of causing the apparatus main body 4 to retreat by a predetermined amount upon distance adjustment to each Purkinje image in the first alignment. However, performing the first alignment at a position retreated in advance by the predetermined amount can omit the operation of causing the apparatus main body 4 to retreat upon temporary approach to the subject's eye. This can shorten the time required for alignment and avoid any discomfort and the risk of contact caused when the distal end of the nozzle approaches the subject's eye.

In the first alignment using each Purkinje image as a reference, because Purkinje images are formed at different positions depending on the curvatures of the corneas, it is not possible to accurately adjust the apparatus main body to the distance to the vertex of the cornea of the subject's eye E of each of different subjects. This is because there are individual differences in corneal curvature. That is, the corneal curvature radii r are distributed in the range of about 7 mm to 9 mm. In the case of the cornea with r of 7 mm, the vertex of the cornea is located 3.5 mm before the reflection image position. In the case of the cornea with r=9 mm, the vertex of the cornea is located 4.5 mm before the reflection image position. With only the first alignment with reference to each Purkinje image with an unknown corneal curvature, the vertex position of the cornea is expected to have an error of 1 mm. Because the alignment tolerance of a general non-contact tonometer is preferably equal to or less than ±0.5 mm, the above operation cannot achieve sufficient alignment.

The following is brief descriptions of the first alignment performed by the first alignment detection unit 71 and the second alignment performed by the second alignment detection unit 72.

<First Alignment>

In the first alignment, the first alignment detection unit 71 causes the light source lighting control unit 75 to turn on the infrared source 21 of the infrared irradiation system 20. This embodiment commonly uses the infrared irradiation system 20 for the first alignment and intraocular pressure measurement, and properly adjusts the luminance of the infrared source 21 in each processing. Note that different illumination optical systems can be used in the respective processing.

When infrared light from the infrared irradiation system 20 enters the cornea, a virtual image (Purkinje image) is generated at the r/2 position of the cornea. In this case, the face cameras 41 and 42 capture images of this Purkinje image, and the relative positions of the air puff nozzle 8 of the apparatus main body 4 and the Purkinje images of the subject's eye E are detected from the positional relationship between the two Purkinje images obtained by the face cameras 41 and 42. The driving unit 50 then moves the apparatus main body 4 in the X, Y, and Z directions to execute the first alignment. However, this first alignment has been performed for each Purkinje image, and hence the distance between the vertex position of the cornea and the distal end of the air puff nozzle 8 is not necessarily proper.

The following will describe the relationship between the position of the subject's eye E relative to the apparatus main body 4 and the positions of the Purkinje images acquired by the face cameras 41 and 42. FIGS. 5A to 7C are schematic views showing the relationship between photographed images and the positions of the subject's eye relative to the photographing devices of the non-contact tonometer.

Figure 5A:
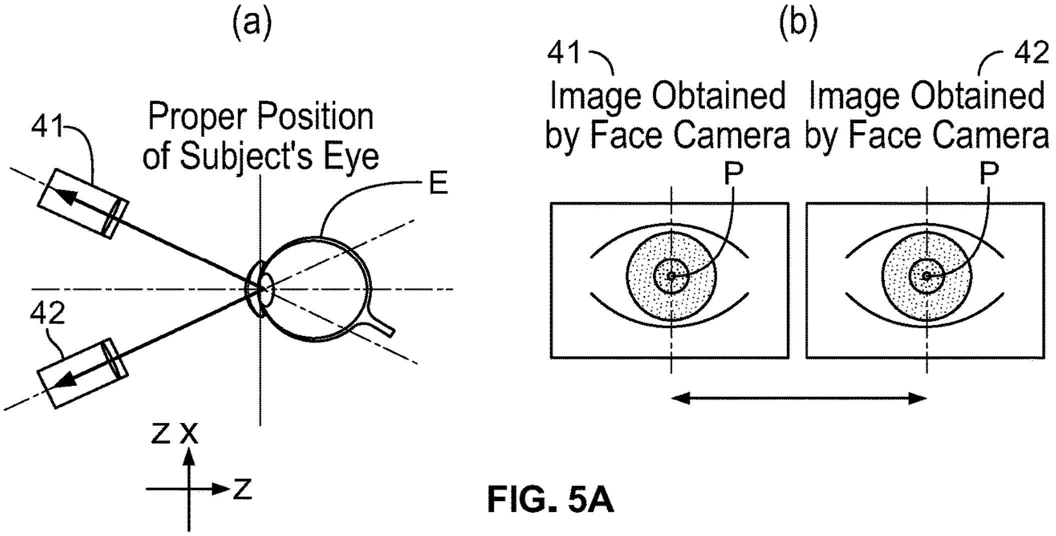
FIGS. 5A to 5C are schematic views showing the relationship between photographed images and the position of a subject's eye relative to the photographing devices of the non-contact tonometer.

The distance between the subject's eye E and the distal end of the air puff nozzle 8 will be described first with reference to FIGS. 5A to 5C. The optical axes of the face cameras 41 and 42 are arranged to intersect with each other at a proper position for alignment. As indicated by (a) in FIG. 5A, the subject's eye E is located at a proper position relative to the apparatus main body 4, that is, properly aligned in the X and Y directions and at a proper distance in the Z direction. In this case, as indicated by (b) in FIG. 5A, Purkinje images P acquired by the face cameras 41 and 42 are located at the middle positions of the respective images.

Figure 5B:
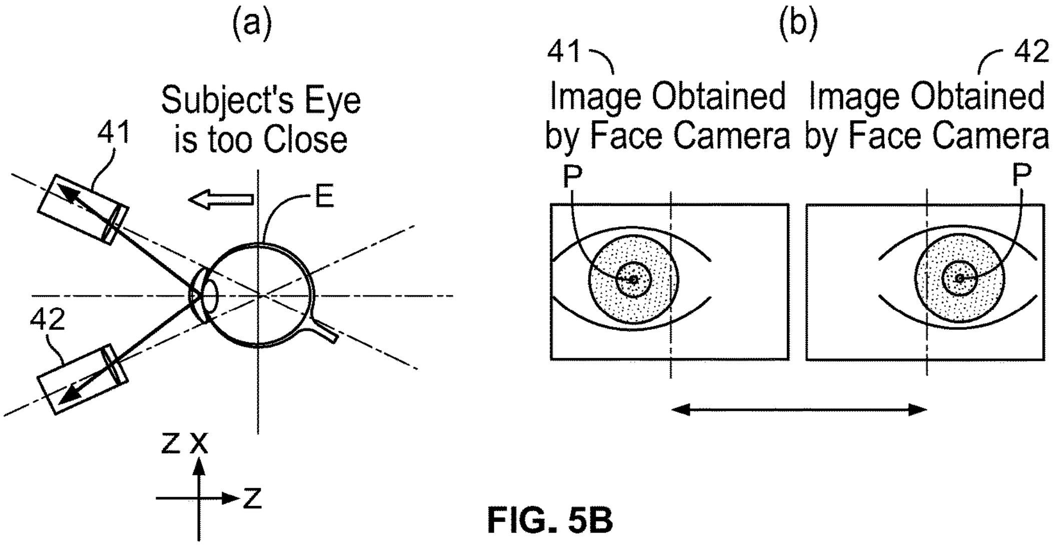

In contrast, when the subject's eye E is located near the apparatus main body 4 as indicated by (a) in FIG. 5B, the Purkinje images P acquired by the face cameras 41 and 42 are located outside the middle positions of the respective images as indicated by (b) in FIG. 5B.

Figure 5C:
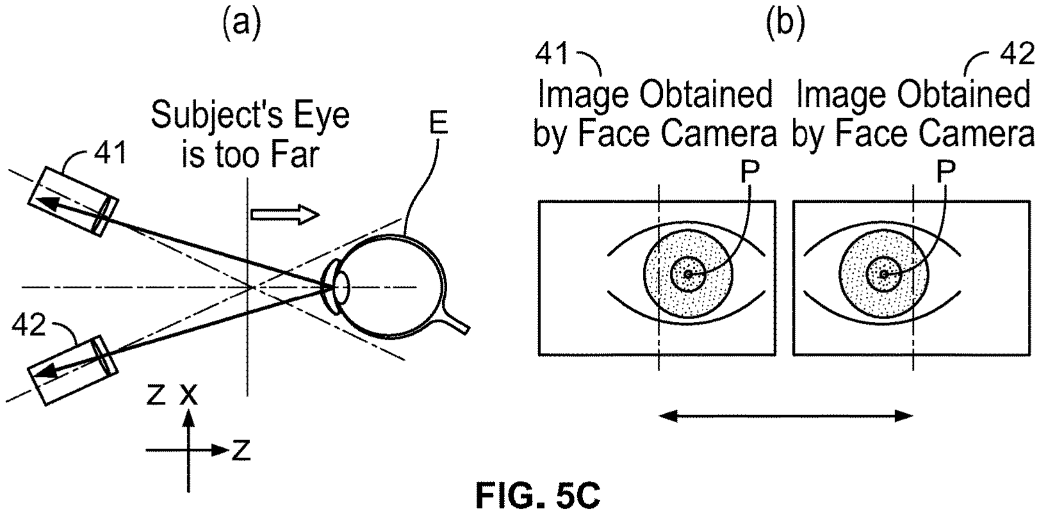

In addition, when the subject's eye E is located far from the apparatus main body 4 as indicated by (a) in FIG. 5C, the Purkinje images acquired by the face cameras 41 and 42 are located inside the middle positions of the respective images as indicated by (b) in FIG. 5C.

Figure 6A:
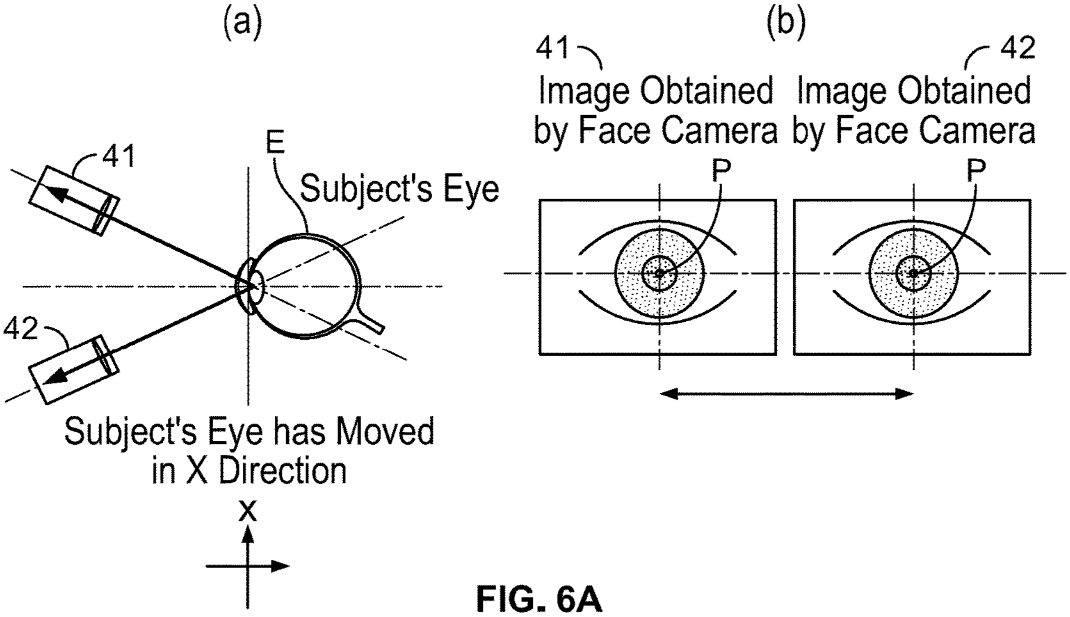
FIGS. 6A to 6C are schematic views showing the relationship between photographed images and the position of a subject's eye relative to the photographing devices of the non-contact tonometer.

A case in which the subject's eye E is shifted in the X and Y directions will be described next with reference to FIGS. 6A to 6C. As indicated by (a) in FIG. 6A, the subject's eye E is located at a proper position relative to the apparatus main body 4, that is, properly aligned in the X and Y directions and at a proper distance in the Z direction. In this case, as indicated by (b) in FIG. 6A, the Purkinje images P acquired by the face cameras 41 and 42 are located at the middle positions of the respective images.

Figure 6B:
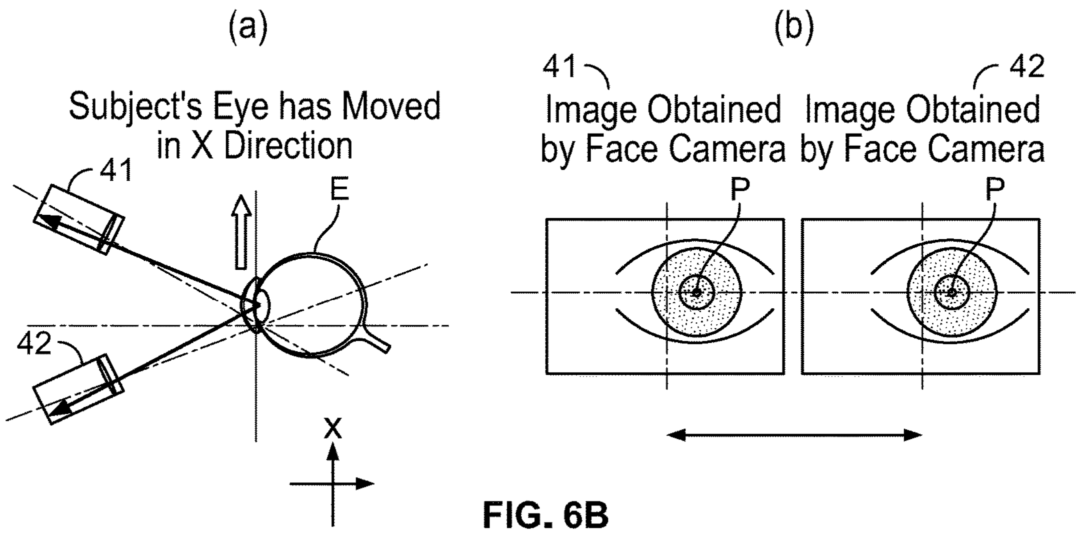

In contrast, when the subject's eye E is shifted relative to the apparatus main body 4 in the X direction as indicated by (a) in FIG. 6B, the Purkinje images P acquired by the face cameras 41 and 42 are shifted relative to the middle positions of the respective images in the same lateral direction as indicated by (b) in FIG. 6B.

Figure 6C:
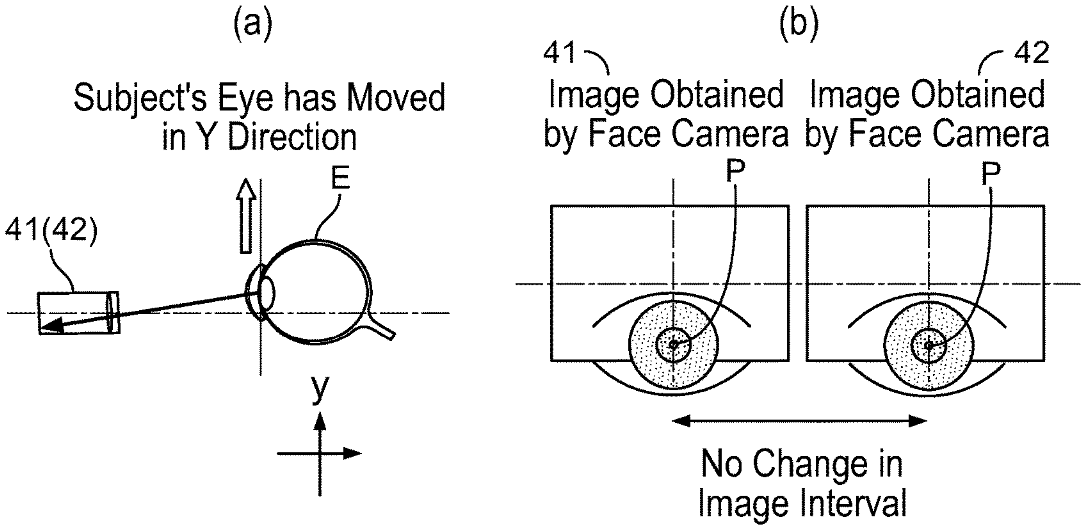

In addition, when the subject's eye E is shifted relative to the apparatus main body 4 in the Y direction as indicated by (a) in FIG. 6C, the Purkinje images acquired by the face cameras 41 and 42 are shifted relative to the middle positions of the respective images in the same vertical direction as indicated by (b) in FIG. 6C.

Figure 7A:
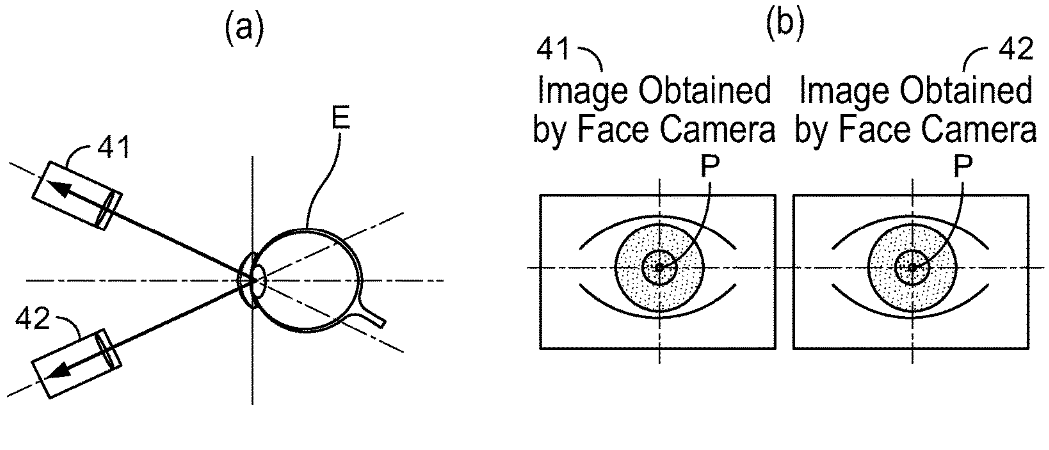
FIGS. 7A to 7C are schematic views showing the relationship between photographed images and the position of a subject's eye relative to the photographing devices of the non-contact tonometer.
Figure 7B:
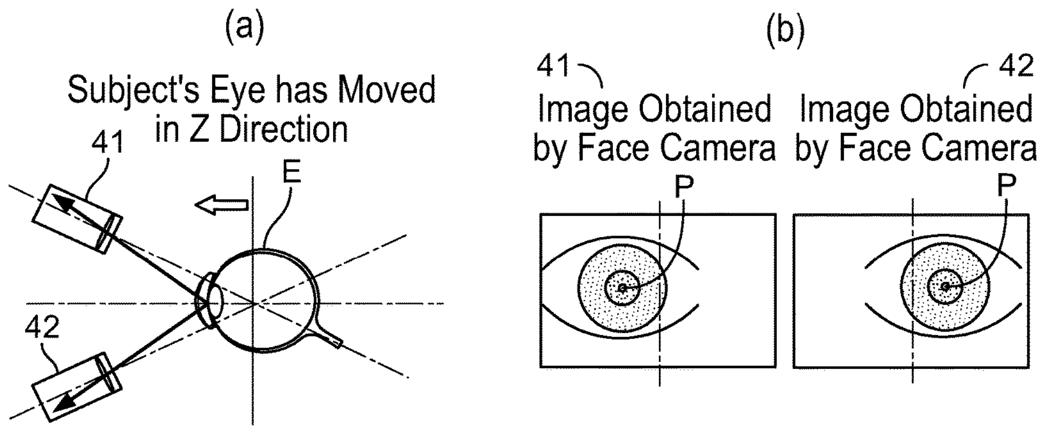
Figure 7C:
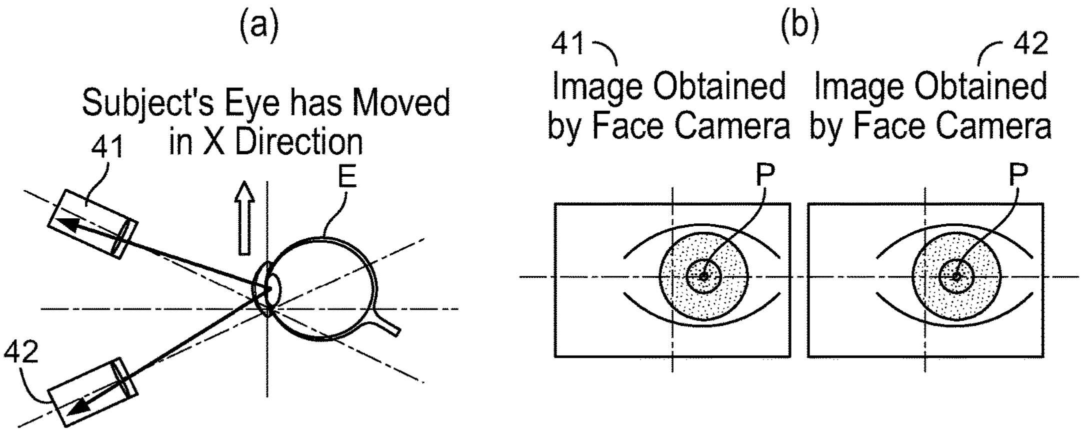

Note that using only an image from one face camera does not allow discrimination between movement in the X direction and movement in the Z direction. In the images ((b) in FIG. 7B and (b) in FIG. 7C) acquired by one face camera 42, the state in which the subject's eye E shown in FIG. 7B has approached the apparatus main body 4 from the alignment state shown in FIG. 7A is identical to the state in which the subject's eye E shown in FIG. 7C has moved in the X direction. Only considering together with the images ((a) in FIG. 7B and (a) in FIG. 7C) acquired by the other face camera 41 enables determining the specific direction in which the subject's eye has moved. Note that the optical axes of the face cameras 41 and 42 need not always intersect with each other at a proper position for alignment and may be located in arbitrary directions. Such cases are handled by performing calibration concerning the relative positions of the cameras and the angles of the optical axes and correcting the positions and moving amounts of images on the cameras.

<Second Alignment>

The second alignment performed by the second alignment detection unit 72 will be described next. When performing the second alignment, the second alignment detection unit 72 causes the light source lighting control unit 75 to turn off the infrared source 21 of the infrared irradiation system 20 and turn on the visible light source 31 of the visible light irradiation system 30. In this case, the visible light irradiation system 30 is also used for visual fixation, and the luminance of the visible light source 31 is adjusted because it has already been turned on for visual fixation. Note that different optical systems may be respectively provided for visual fixation and the second alignment.

Figure 8B:
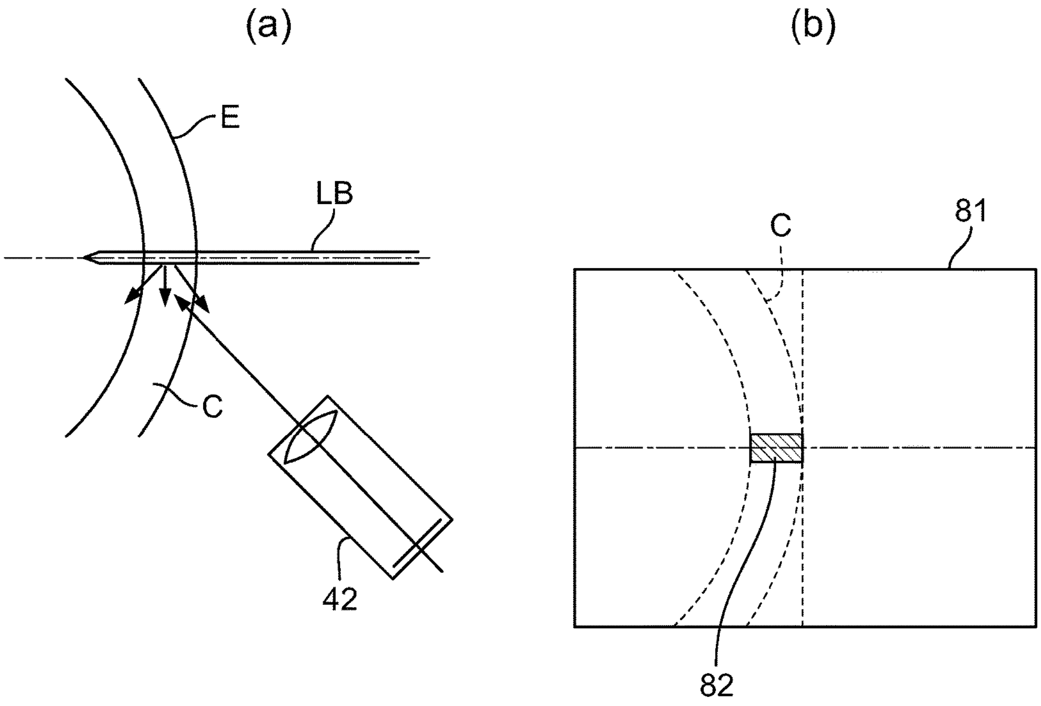

As indicated by (a) in FIG. 8B, a visible light beam LB from the visible light irradiation system 30 enters a cornea C of the subject's eye E and is transmitted through the cornea C. At this time, part of the light beam LB is scattered by tissue in the cornea C. The face camera 42 receives this scattered light to enable the observation of the light. A scattered light image 82 of the cornea C appears in an image 81 acquired by the face camera 42. This detects the position of the captured scattered light image, more specifically, the vertex position of the cornea. Note that because this scattered light is darker than the Purkinje image, the gain of the face camera 42 is increased in advance.

The second alignment uses one of the face cameras 41 and 42 used for the first alignment, for example, the face camera 42. Note that the face camera 42 to be used may have arbitrary imaging properties such as magnification and photographing angle as long as they are known.

In this case, the light emitted by the visible light source 31 of the visible light irradiation system 30 is scattered by the cornea more as the wavelength becomes shorter. For this reason, the visible light source 31 is preferably a blue light source. In order to prevent illumination light and the like in the room from entering the face cameras 41 and 42 to cause ghost and flare and affecting the detection of Purkinje images and scattered light images, it is preferable to install transmission filters in front of the face cameras 41 and 42. These filters are designed to transmit only wavelengths near the wavelength of infrared light used for the first alignment and wavelengths near the specific wavelength of visible light (for example, blue light) used for the second alignment and do not transmit other wavelengths by reflecting and absorbing them.

The detection of alignment states in the three X, Y, and Z directions requires at least two face cameras. One face camera may be used in completing alignments in the X and Y directions, which are free from the influence of the corneal curvature, in the first alignment and performing only adjustment in the Z direction in the second alignment.

Note that one photographing device of the two face cameras 41 and 42, for example, the face camera 41, may be placed on an angle matching the axis O1 as a measurement optical axis. At least one of images of the anterior eye part obtained by the face cameras 41 and 42 is displayed on the screen of the monitor 6. This allows the measurer to observe the state of the subject's eye.

When executing alignment by a manual operation, the measurer can perform alignment based on the above image. Such an image may be the one directly acquired from one camera, the one processed to look like as if it were seen squarely in almost real time, or the like. In manually performing alignment, it is preferable to arrange infrared sources for illuminating the anterior eye part near the face cameras 41 and 42 so as to allow the observation of images of the anterior eye part on the monitor. In addition, in manually executing alignment, an alignment mark as a reference for alignment and an indication indicating an alignment shift in the longitudinal direction are superimposed and displayed on each image of the anterior eye part.

<Basic Operation Procedure of Non-Contact Tonometer>

Figure 9:
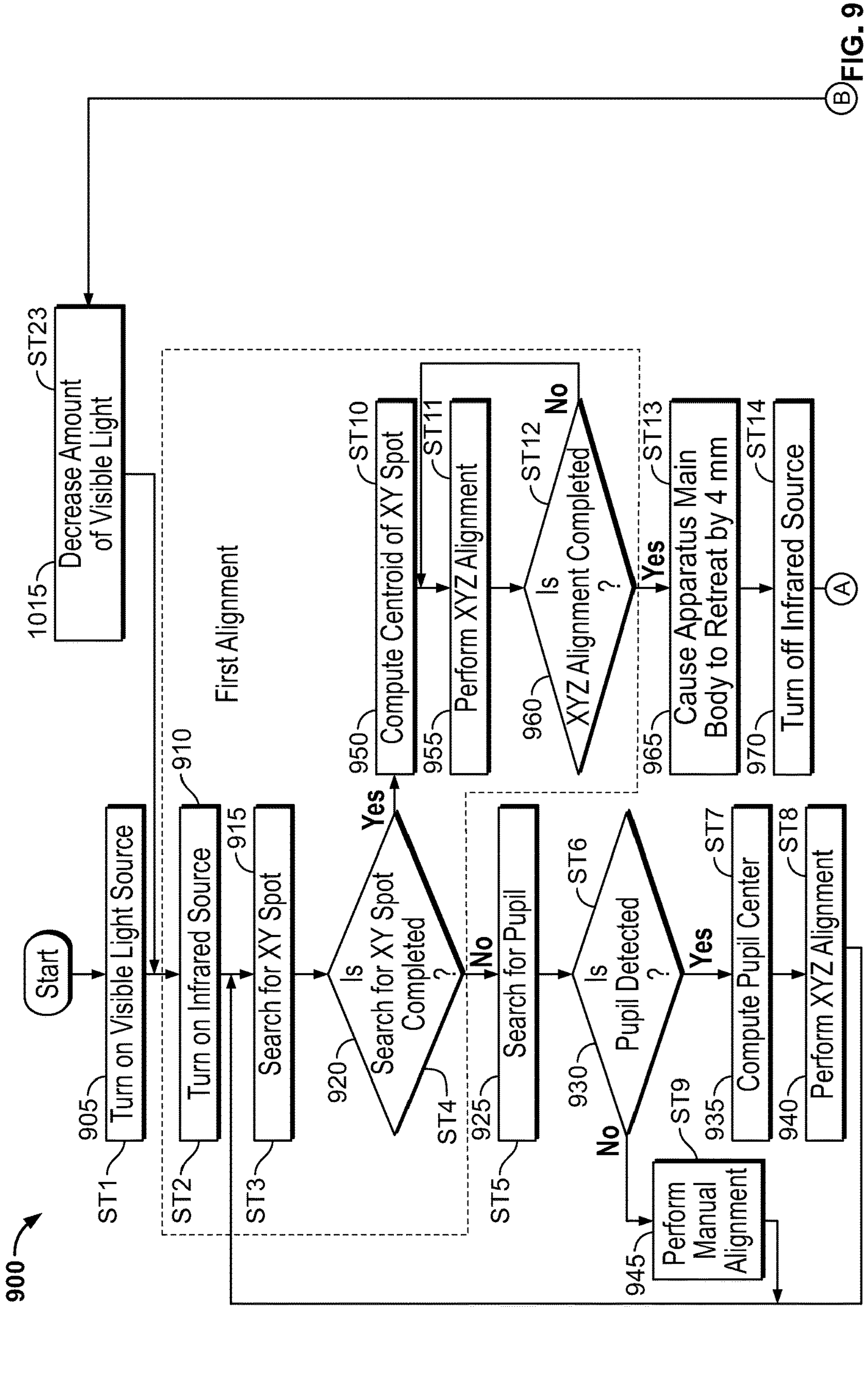
FIG. 9 is a flowchart showing a basic operation procedure of the non-contact tonometer.
Figure 9:
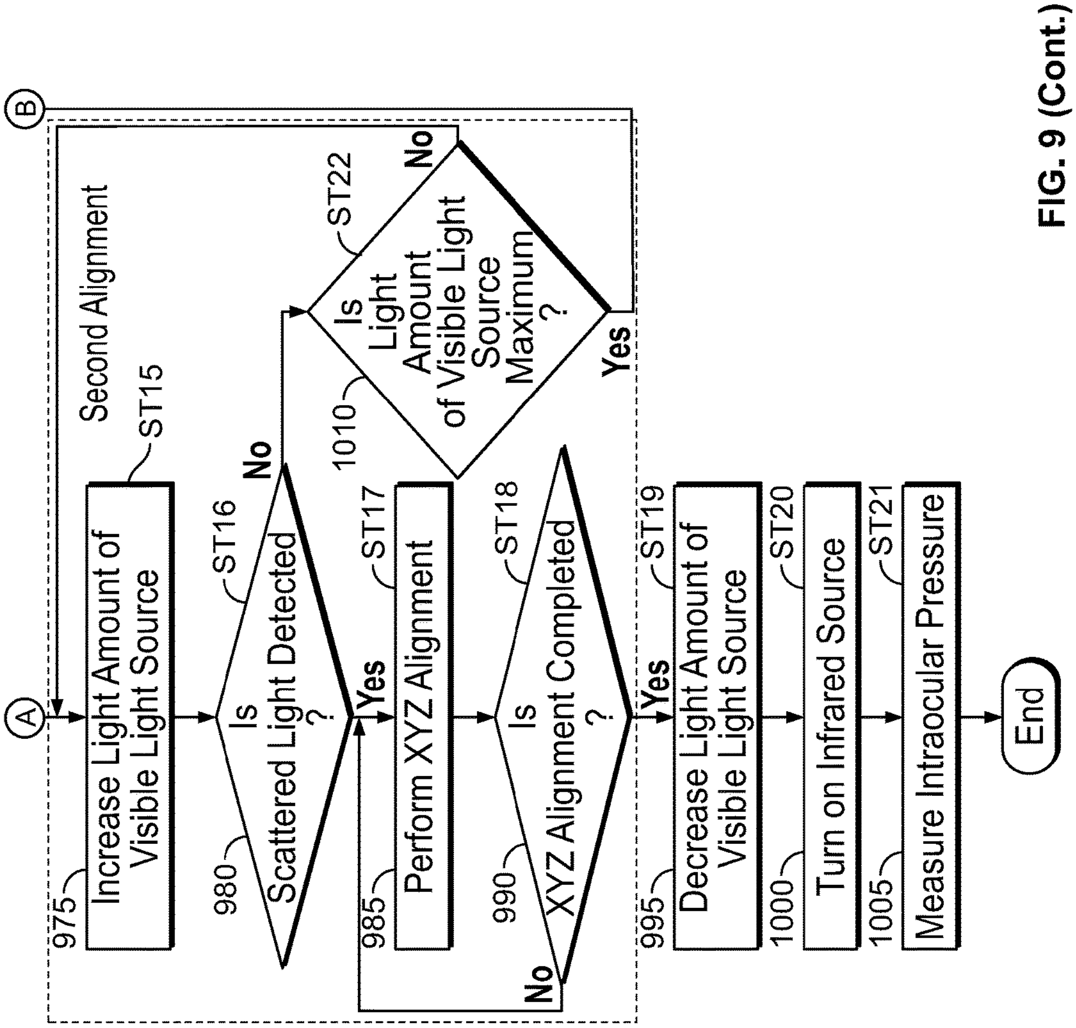

An intraocular pressure measurement procedure will be described in detail below. FIG. 9 is a flowchart 900 showing the operation procedure of the non-contact tonometer. First of all, in the non-contact tonometer S, the light source lighting control unit 75 of the control unit 70 turns on the visible light source 31 of the non-contact tonometer S to irradiate the subject's eye E with fixation light at step 905 (also referred to herein as step ST1). The light source lighting control unit 75 then turns on the infrared source 21 to illuminate the subject's eye E with infrared light at step 910 (also referred to herein as step ST2). This makes the face cameras 41 and 42 capture Purkinje images of the subject's eye E. The first alignment detection unit 71 then acquires these images.

The first alignment detection unit 71 drives the driving unit 50, based on these images, to perform the first alignment. In this embodiment, the first alignment detection unit 71 detects an XY spot (Purkinje image) in the subject's eye E for performing the first alignment at step 915 (also referred to herein as step ST3). Upon detecting an XY spot at step 920 (also referred to here as step ST4; YES in step ST4), the first alignment detection unit 71 performs alignment in the X and Y directions as step 950 (also referred to herein as step ST10) and distance adjustment in the Z direction (XYZ alignment) at steps 955 and 960 (also referred to herein as steps ST10 and ST11, respectively).

Upon detecting no XY spot (NO in step ST4), the first alignment detection unit 71 searches the images acquired by the face cameras 41 and 42 for the pupil at step 925 (also referred to herein as step ST5). The first alignment detection unit 71 detects the pupil first, and then detects Purkinje images. Upon detecting the pupil at step 930 (also referred to herein as step ST6; YES in step ST6), the first alignment detection unit 71 computes the central position of the pupil at step 935 (also referred to herein as step ST7), and performs XYZ alignment at step 940 (also referred to herein as step ST8). This usually makes it possible to detect an XY spot.

If the first alignment detection unit 71 cannot detect the pupil (NO in step ST6), the examiner manually performs alignment at step 945 (also referred to herein as step ST9). The process then returns to the step of searching for an XY spot at step 915 (step ST3). The pupil cannot be obtained when the face cameras 41 and 42 capture images of part of the face HB other than the subject's eye E because the support portion 1 is not properly adjusted relative to the face HB. The examiner adjusts the height of the support portion 1 so as to properly place the face HB of the subject on the support portion 1. Furthermore, the examiner operates the operation knob 5 to drive the driving unit 50 and move the apparatus main body 4 while observing the monitor 6, thus performing alignment to enable the observation of the subject's eye E through the face cameras 41 and 42. In this manual alignment, illumination devices arranged near the face cameras 41 and 42 emit infrared light.

While an XY spot is detected (YES in step ST4), the first alignment detection unit 71 computes the centroid of the XY spot (step ST10). The drive control unit 73 then causes the drive control unit 73 to drive the driving unit 50 based on the obtained centroid and performs XYZ alignment of the air puff nozzle 8 with respect to the subject's eye E (steps ST11 and ST12).

While XYZ alignment is completed (YES in step ST12), the air puff nozzle 8 has not yet been at a proper position with respect to the subject's eye E. For this reason, the drive control unit 73 causes the second alignment detection unit 72 to drive the driving unit 50 so as to make the air puff nozzle 8 retreat by 4 mm at step 965 (also referred to herein as step ST13), and stops irradiation with infrared light at step 970 (also referred to herein as step ST14).

The non-contact tonometer S then performs the second alignment. First of all, the light source lighting control unit 75 increases the luminance of the visible light source 31 at step 975 (also referred to herein as step ST15). Visible light from the visible light source 31 is scattered in the cornea of the subject's eye E, and the face camera 41 acquires the scattered light image at step 980 (also referred to herein as step ST16). Upon failing to acquire any scattered light image, the light source lighting control unit 75 maximizes the luminance of the visible light source 31 to acquire a scattered light image in the same manner as described above.

Upon acquiring a scattered light image (NO in step ST16), the second alignment detection unit 72 acquires the vertex position of the cornea. The drive control unit 73 then moves the apparatus main body 4 based on the acquired cornea position, thus adjusting the position of the air puff nozzle 8 at steps 985 and 990 (also referred to herein as steps ST17 and ST18, respectively). Upon completion of the positional adjustment of the apparatus main body 4 (YES in step ST18), the light source lighting control unit 75 decreases the luminance of the visible light source 31 as step 995 (also referred to herein as step ST19) and turns on the infrared source 21 at step 1000 (also referred to herein as step ST20). In this state, the intraocular pressure measurement control unit 74 drives the air spray device 60 to puff air from the air puff nozzle 8 to the subject's eye E, and causes the applanation sensor 17 to detect reflected light, thus measuring an intraocular pressure at step 1005 (also referred to herein as step ST21).

Upon failing to detect any scattered light (NO in step ST16), the second alignment detection unit 72 causes the light source lighting control unit 75 to determine whether the luminance of the visible light source 31 is maximum at step 1010 (also referred to herein as step ST22). If the luminance is not maximum (NO in step ST22), the light source lighting control unit 75 increases the luminance of the visible light source 31 to detect scattered light again (step ST15). If the luminance of the visible light source is maximum (YES in step ST22), the light source lighting control unit 75 decreases the luminance of the visible light source 31 at step 1015 (also referred to herein as step ST23) to make alignment setting again from the first alignment setting.

As described above, the non-contact tonometer S according to this embodiment performs the first alignment to align the position of the air puff nozzle 8 relative to the subject's eye E in the X and Y directions and in the Z direction based on Purkinje images. Upon temporarily making the apparatus main body 4 retreat, the non-contact tonometer S performs the second alignment to detect the vertex position of the cornea and align the air puff nozzle 8 with the vertex of the cornea in the Z direction. This allows the non-contact tonometer S to directly detect the vertex of the cornea of the subject's eye E, and hence eliminates the necessity of consideration of differences in anterior chamber depth or corneal curvature among subjects.

Second Embodiment

Figure 10A:
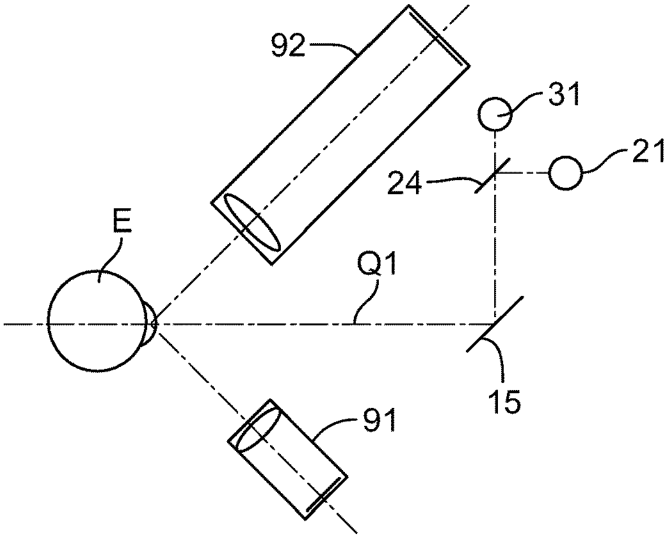
FIGS. 10A to 10C are schematic views for explaining a non-contact tonometer according to the second embodiment of the present invention.
Figure 10B:
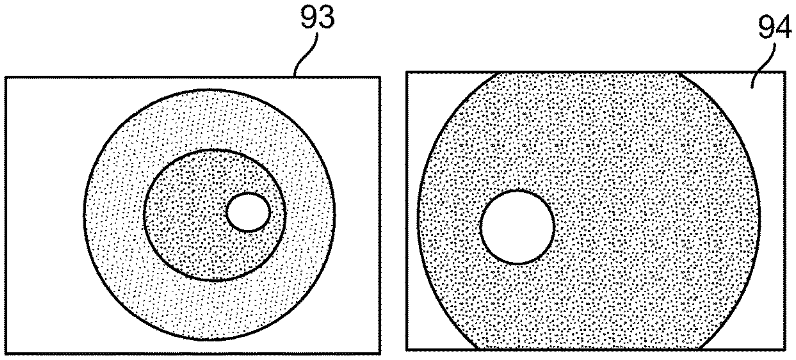
Figure 10C:
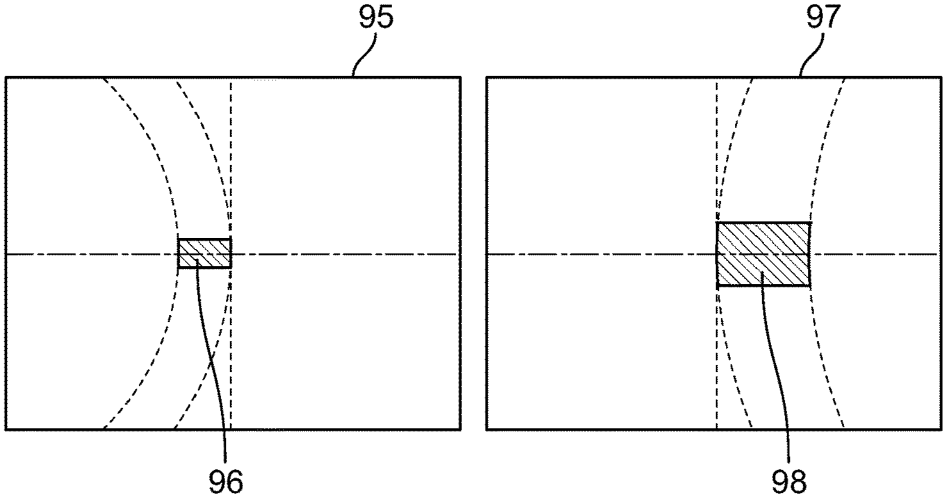

In the above embodiment, the face cameras 41 and 42 have the same magnification. In the second embodiment, at least one of two face cameras has a larger photographing magnification than the other photographing device. FIGS. 10A to 10C are schematic views for explaining a non-contact tonometer according to the second embodiment of the present invention. In this case, a face camera 92 has a larger photographing magnification than a face camera 91. For this reason, as shown in FIG. 10B, although a whole subject's eye E appears in a photographed image 93 obtained by the face camera 91, an enlarged image of the pupil of the subject's eye E appears in a photographed image 94, originating from infrared light, obtained by the face camera 92. Note, however, that when the observation magnification is increased, the range in which the camera can photograph is narrowed. For this reason, in order to set the same observation range as that of a low-magnification camera, it is preferable to use a camera with the ratio between the respective sides of the effective imaging area of the sensor being equal to or more than the ratio between the photographing magnifications described above. In addition, to avoid a decrease in resolution, the pixel pitch of the sensor is preferably equal to or less than the photographing magnification ratio.

When the subject's eye is irradiated with a visible light beam in this state, a cornea scattered light image 98 of a photographed image 97 obtained by the face camera 92 is larger than a cornea scattered light image 96 of a photographed image 95 obtained by the face camera 91, as shown in FIG. 10C. In this embodiment, performing the second alignment using the high-magnification face camera 92 can acquire the vertex position of the cornea with high accuracy. In this case, the low-magnification face camera 91 is not used for imaging visible light, and hence may use a transmission filter which transmits only infrared light. This makes it possible to reduce the number of expensive two-region transmission filters to be used and prevent an increase in cost.

Note that the first embodiment performs Z alignment by detecting the vertex position of the cornea using one face camera in the second alignment. Note that the present invention enables the detection of the vertex of the cornea by using the two face cameras 41 and 42. In this case, the vertex position of the cornea can be specified in the X, Y, and Z directions, and both XY alignment and Z alignment can be executed in the second alignment.

In actual measurement, after the completion of the first alignment, XY alignment sometimes deteriorates as the subject's eye E moves during the second alignment. Assume that XY alignment cannot be performed only in the first alignment. In this case, when the subject's eye E moves, the second alignment (Z alignment) must be performed after the first alignment (XY alignment) is performed again. In some instances, the first alignment and the second alignment must be performed alternately. In contrast to this, photographing using the two face cameras 41 and 42 in the second alignment makes it possible to specify the vertex position of the cornea in the X, Y, and Z directions and execute both XY alignment and Z alignment. This eliminates the need to perform the first alignment again.

What is claimed is:

1. An ophthalmic apparatus comprising:

an apparatus main body including an infrared irradiation system configured to irradiate a subject's eye with infrared light and an infrared detection system configured to detect the infrared light from the subject's eye;

a support portion configured to support a position of the face of a subject from the subject's eye;

a driving unit configured to align an axis of the apparatus main body with the subject's eye and also perform distance adjustment of the apparatus main body to the subject's eye by relatively moving the apparatus main body and the support portion;

a visible light irradiation system placed coaxially with the apparatus main body and configured to irradiate the subject's eye with visible light;

not less than two photographing devices configured to substantially simultaneously photograph the subject's eye from different directions;

a first alignment detection unit configured to acquire Purkinje images of the subject's eye, originating from the infrared light, from not less than two photographed images of the subject's eye obtained by the two photographing devices and detect a position of the subject's eye from the Purkinje images;

a second alignment detection unit configured to acquire a scattered light image of a cornea of the subject's eye, originating from the visible light, obtained by at least one of the two photographing devices and detect a vertex of the cornea based on the scattered light image; and a drive control unit configured to align the apparatus main body with the subject's eye by controlling the driving unit based on a detection result obtained by the first alignment detection unit and also perform distance adjustment or alignment and distance adjustment of the apparatus main body with respect to the subject's eye by controlling the driving unit based on a detection result obtained by the second alignment detection unit.

2. The apparatus according to claim 1, wherein the scattered light image of the cornea is acquired by one of the not less than two photographing devices.

3. The apparatus according to claim 1, wherein at least one photographing device of the not less than two photographing devices has a larger photographing magnification than another or other photographing devices.

4. The apparatus according to claim 1, wherein the photographing device comprises a transmission filter configured to transmit the infrared light.

5. The apparatus according to claim 1, wherein the photographing device of the photographing devices which obtains the scattered light image of the cornea comprises a transmission filter configured to transmit the infrared light and the visible light.

6. The apparatus according to claim 1, wherein the infrared irradiation system is configured to change an intensity of infrared light for irradiation.

7. The apparatus according to claim 1, wherein the visible light irradiation system is configured to change an intensity of the visible light for irradiation.

8. An alignment method for an ophthalmic apparatus which includes an apparatus main body configured to irradiate a subject's eye with infrared light and also detect the infrared light from the subject's eye, a support portion configured to support a position of the face of a subject, and a driving unit configured to relatively move the apparatus main body and the support portion, aligns the apparatus main body with the subject's eye by relatively moving the apparatus main body and the support portion, and performs distance adjustment with respect to the subject's eye, the method comprising:

detecting Purkinje images of the subject's eye by substantially simultaneously photographing a cornea of the subject's eye from not less than two different directions by irradiating the subject's eye with infrared light;

aligning the apparatus main body with the subject's eye based on positions of the Purkinje images;

detecting a scattered light image of the cornea, originating from visible light which has irradiated the subject's eye; and performing distance adjustment or alignment and distance adjustment of the apparatus main body with respect to the subject's eye based on a vertex of the cornea of the subject's eye detected based on the scattered light image.

* * * * *